United States Patent [19]

Moscetta

[11] Patent Number: 5,411,708
[45] Date of Patent: May 2, 1995

[54] APPARATUS FOR THE DETERMINATION OF ANALYTES IN LIQUID SAMPLES

[76] Inventor: Pompeo Moscetta, 186 Via Eschilo, I-00125 Casalpalocco RM, Italy

[21] Appl. No.: 39,101
[22] PCT Filed: Aug. 5, 1992
[86] PCT No.: PCT/IT92/00093
§ 371 Date: Apr. 6, 1993
§ 102(e) Date: Apr. 6, 1993
[87] PCT Pub. No.: WO93/03345
PCT Pub. Date: Feb. 18, 1993

[30] Foreign Application Priority Data

Aug. 6, 1991 [IT] Italy .................. RM91A0601

[51] Int. Cl.$^6$ .................. G01N 35/08; G01N 35/10
[52] U.S. Cl. .................. 422/81; 422/68.1; 436/43; 436/180
[58] Field of Search .................. 422/68.1, 81, 82; 436/180, 43

[56] References Cited

U.S. PATENT DOCUMENTS

| | | |
|---|---|---|
| 3,488,154 | 1/1970 | Hronas .................. 422/81 X |
| 3,654,113 | 4/1972 | Bochinski .................. 422/81 X |
| 4,441,374 | 4/1984 | Suzuki .................. 422/81 X |
| 4,680,270 | 7/1987 | Mitsumaki et al. .................. 422/81 X |
| 4,920,056 | 4/1990 | Dasgupta .................. 422/81 X |
| 5,075,080 | 12/1991 | Sanders .................. 422/81 X |
| 5,196,169 | 3/1993 | Schick et al. .................. 422/81 |
| 5,221,521 | 6/1993 | Hashizume et al. .................. 422/81 X |
| 5,230,863 | 7/1993 | Salpeter .................. 422/82 X |

FOREIGN PATENT DOCUMENTS

| | | |
|---|---|---|
| 0001137 | 8/1978 | European Pat. Off. . |
| 0253519 | 6/1987 | European Pat. Off. . |
| 0468896 | 1/1992 | European Pat. Off. . |
| 3215742 | 9/1991 | Japan .................. 422/68.1 |
| 3269349 | 11/1991 | Japan .................. 422/68.1 |

OTHER PUBLICATIONS

Ping et al., "Determination of Urinary Mercury with an Automated Micro Batch Analyzer", Anal. Chem. 62, 1990, 85–88.
Dasgupta et al., "Kinetic Approach to the Measurement of Chemical Oxygen Demand with an Automated Micro Batch Analyzer", Anal Chem. 62, 1990, 395–402.
Sweileh et al., "Applications of In Situ detection with an Automated Micro Batch Analyzer", Anal. Chimica Acta, 214, 1988, 107–120.
Sweileth et al., "New Automated Microbatch Analyser", Review of Scientific Instruments, vol. 59, No. 12, Dec. 1988, New York, US: pp. 2609–2615.
Rios et al., "Multidetection in unsegmented flow systems with a single detector", Analyticl Chemistry, vol. 57, 1985, Columbus, US, pp. 1803–1809.
Calhoun et al., "Application of temporal optimization", vol. 60, 1988, Columbus, US, pp. 549–551.
Betterridge et al., "Control of dispersion and variation of reaction coil length", Analytical Chemistry, 59, 1987, Columbus, US, pp. 1236–1238.

*Primary Examiner*—Donald E. Czaja
*Assistant Examiner*—Milton I. Cano
*Attorney, Agent, or Firm*—Browdy and Neimark

[57] ABSTRACT

An apparatus for the determination of analytes in liquid samples is disclosed. The apparatus comprises in fluid connection a positive-displacement pump, a chamber in which the reagents specific for the analytes to be determined can be delivered, a detector, a second chamber and a device for the introduction of sample within the circuit and for the discharge. The apparatus also provides for apparatus to control flow and to control of the operation of each component. A process for the determination of the analytes is also disclosed.

17 Claims, 2 Drawing Sheets

APPARATUS FOR THE DETERMINATION OF ANALYTES IN LIQUID SAMPLES

DESCRIPTION

The present invention relates to a process for the determination of analytes in liquid samples, and the relative apparatus.

Prior art

In manual practice for performance of chemical analysis, after having defined the reaction chemism and the reagents required for its development, the addition of the reagents to the sample to be analyzed takes place and mixing is performed in order to minimize the molecular diffusion times and thus permit rapid development of the reaction. In the case of colorimetric methods, which are by far the most widely used methods of chemical analysis, development of the reaction brings about a variation in transmittamcy of the range of reaction products with transparency and/or absorption bands on specific wavelengths which can be correlated, after calibration, with the concentration of the parameter being measured.

Many systems have been turned up over the last fifty years with the aim of rendering chemical analysis more and more automatic, a large number of methods allowing said automatization has been tuned up using instruments having the following analytical principles.

C.F.A. Continuous-Flow Analysis
F.I.A. Flow Injection Analysis
D.A. Discrete Analysis These three analytical principles will be briefly analyzed below.

Continuous Flow Analysis

Using this principle, instruments for automatic chemical analysis with innumerable applications have been developed.

In an analytical reactor (Manifold), all the reagents necessary for development of the reaction are continuously added, by means of a positive-displacement pump. The flow of reagents is divided at regular intervals of time (normally approximately two seconds) by air bubbles, so as to define small segments of liquid, which advance under the thrust of the pump. The samples to be analyzed are inserted in sequence, at pre-determined intervals, into the flow of segmented reagents. Contact between the samples and the reagents starts development of the reaction, which is accelerated by mixing, performed dynamically on the previously obtained segments of liquid, which are made to flow through coils of suitable length.

The flow of reagents, mixed with the samples, after having crossed the Manifold, where the reaction has been completely developed, reaches the detector (in the case of colorimetric methods this is obviously a colorimeter, but it can also be any other detector producing an electric signal in proportion to the concentration of the parameter being measured). The methods applying the analytical principle of Continuous Flow Analysis make it possible to carry out tests for End Point reactions (that is to say on complete termination of the reaction) and Kinetic reactions (performing a series of tests as the reaction develops and evaluating the speed at which the parameters measured vary).

Flow Injection Analysis

F.I.A. (Flow Injection Analysis) represents a variation, and in some cases an evolution, of Continuous Flow Analysis, and makes it possible to automate most of the methods developed for C.F.As. All the reagents necessary for development of the reaction are continuously added in the analytic reactor by means of a positive-displacement pump. Unlike Continuous Flow Analysis, in Flow Injection Analysis (F.I.A.) there is no segmentation of the flow. A known volume of sample is injected rapidly into the flow of reagents, giving an extremely marked effect of molecular diffusion and a consequent rapid start of the chemical reaction. The flow of reagents and sample quickly reaches the detector, while the reaction is still under progress. The detector generates an electric signal proportional to the concentration of the parameter being measured.

Discrete Analysis

Discrete analyzers, defined thus as opposed to Continuous Flow ones, have seen formidable development during the last few years, especially in the clinical chemistry sector, and for the most part use the same reaction chemisms developed for Continuous Flow. However, in the Discrete analyzers no particular methodological concepts are used, as is the case in Continuous Flow Analysis or Flow Injection Analysis, as the classical manual methods are re-proposed, with the widest possible range of automations.

The sample and the reagents are placed in a test tube (or the like), and mechanical mixing is performed using a wide variety of techniques. After the time required for development of the reaction, the product of said reaction is measured using a detector.

These discrete analyzers make it possible to perform End Point, Kinetic and Fixed Time measurements (with a measurement taken at a point in time corresponding to a predetermined state of development of the reaction). They are particularly versatile, and easily permit correction of sample blank and reagent dblank (that is to say subtraction of the contribution given by the sample and reagent matrix to the final optical density measured by the instrument) and calibrations using internal standard (known additions of solution at a known concentration).

Most of these analyzers belonging to the state of the art and designed mainly for the clinical sector, have detection limits insufficient for the analytic requirements of many fields.

These apparatuses are of notable mechanical size, which do not allow easy transport or equally easy use for on site analysis, and this remains their main disadvantage. This can be easily understood, when considering that a single Discrete analysis module, for the determination of a single chemical parameter, can easily exceed a weight of 100 Kg, when complete with reagents. Modules for Discrete Analysis have also been used for completely automatic industrial monitoring.

The analytic systems described above showed are not only limited regarding detection and type of reaction, but are also unsuitable, for application to environmental monitoring systems, for example the monitoring of oceans, rivers, lakes, the air and industrial waste disposal areas, said applications being connected to an increasingly widespread need for miniaturization, in any case, due to their large dimensions and the consequent difficulties of transport and positioning. Furthermore, another disadvantage encountered in the devices known to the state of the art is the high consumption of reagents and electricity, which consequently causes logistic problems.

It has now been surprisingly found that a process embodying a new analytical measurement cycle can overcome the disadvantages affecting processes according to the state of the art, in particular as regards the need for miniaturization of the instrumentation and its transportability and ease of installation, while at the same time consuming minimal quantities of reagents. Furthermore, according to the process object of the present invention, it is possible to reach detection limits lower than those obtainable through the methods known from the state of the art.

An object of the present invention is therefore to provide a process for the determination of analytes in liquid samples, characterized in that it comprises the following steps:

a) sampling of a liquid sample containing the analytes to be determined within a measuring circuit;

b) additioning to said liquid sample specific reagents specific for said analytes and/or calibrators;

c) mixing of said liquid sample with said reagents and/or said calibrators;

d) determination of the concentration of said analytes; and e) discharging said liquid sample containing said analytes, said reagents and/or calibrators.

A further object of the present invention is to provide an apparatus for carrying out the determination of analytes in liquid samples, characterized in that it comprises in "liquid connection" and in succession:

a) sampling means;

b) bidirectional pump means;

c) first container means for the liquid sample;

d) means for the controlled addition of reagents and/or calibrators into said first container means;

e) means for interruption of the liquid connection;

f) means for the determination of the concentration of said analytes;

g) second container means for the liquid sample;

h) discharge means for said liquid sample and reagents and/or calibrators; and i) means for adjusting and controlling the apparatus, whereby a continually repeated circulation of said liquid sample within said apparatus is obtained.

Further objects and advantages of the present invention will be more clearly seen from the following description of a preferred embodiment of the invention itself.

BRIEF DESCRIPTION OF THE DRAWINGS

With the present description are enclosed No. 2 plates of figures, in which.

DESCRIPTION OF A PREFERRED EMBODIMENT OF THE INVENTION

Figure 1:
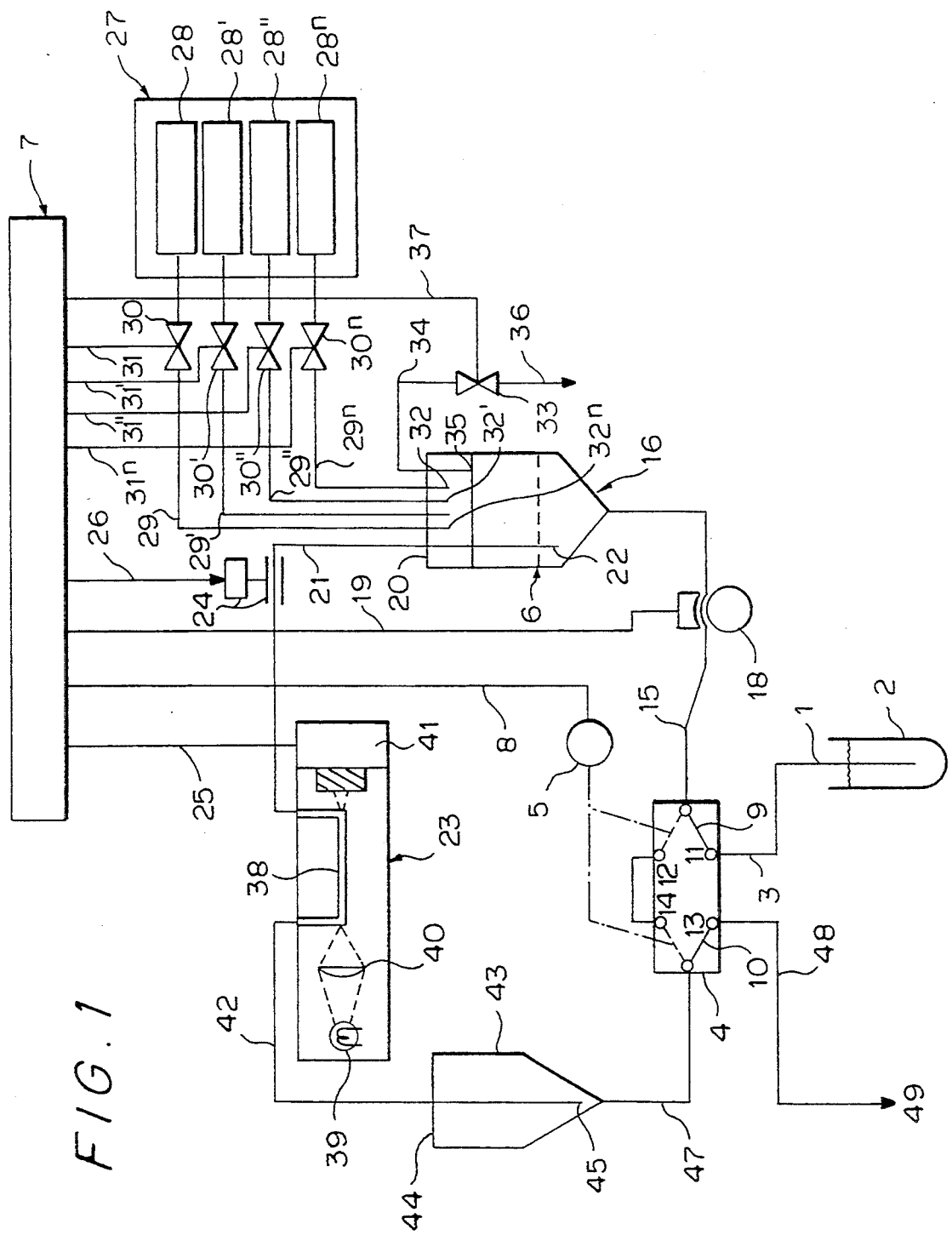
FIG. 1 shows a schematic view of the apparatus according to the present invention.

With reference to FIG. 1, an apparatus according to the present invention is shown therein. A substantially tubular sampling thief 1 with open ends, or another means for taking samples, draws from a flask 2 (or other equivalent container) containing the sample a quantity of the same. The sampling thief 1 can also be directly connected to the sample material for continuous monitoring. The sampling thief 1 is connected at one end to a tube 3, the other end of said tube being connected to a four-way valve 4 driven by a motor 5. A programmer 7 has an output 8 connected to the motor 5 to control its operation. Following actuation of the motor 5, the switch members 9 and 10 are moved from positions 11 and 13 to positions 12 and 14, respectively for the sampling, analysis and discharge operations.

The valve 4 is connected by means of a tube 15 to the bottom of a chamber 16. The tube 15 is operatively associated with a peristaltic pump 18 and cooperates with said pump to displace the liquid samples within the apparatus. An output 19 of the programmer 7 is connected to the peristaltic pump 18 for the actuation of the same. The actuation mode of the pump can define within the circuit of the apparatus according to the present invention a "clockwise" flow direction, from valve 4 towards chamber 16, and a "counterclockwise" flow direction when the liquid within the apparatus according to the present invention is displaced from the chamber 16 towards the valve 4.

A tube 21 is inserted into the chamber 16 through the cover 20, the end 22 of said tube draws fluid from within said chamber 16. Said chamber 16 and said cover 20 are sealingly assembled together, i.e. in such a way as to allow an overpressure or negative pressure to be maintained within said chamber. The tube 21 connects the chamber 16 to the colorimeter 23 and is operatively associated with the fluid cut-off valve 24. The colorimeter can be substituted by another type of detector, without departing from the scope of the present invention. Examples of suitable detectors are photometric, colorimetric, nephelometric, conductometric and/or selective ion detectors. Further, according to the type of determination and the analyte to be determined there can be provided reduction columns, thermostated coils, dialysis units, distillation columns, ionic exchange resins, etc..

An output 25 and an output 26 of the programmer 7 are connected, respectively, to the colorimeter 23 for signal acquisition and to the cut-off valve 24 for its actuation. A reagent container 27 is placed close to the chamber 16 to cooperate therewith. The container 27 holds a number of compartments 28, 28' . . . 28n for reagents or calibrators, said compartments being connected by means of a number of tubes 29, 29' . . . 29n to the chamber 16 through the cover 20, for the delivery of reagents and/or calibrators, respectively.

Each tube 29, 29' . . . 29n cooperates with a respective cut-off valve 30, 30' . . . 30n to adjust and command the delivery of reagents. A number of outputs 31, 31' . . . 31n of the programmer 7 are connected respectively to each valve 30, 30' . . . 30n for their actuation in order to command the consequent delivery of reagents. A second valve 33 is arranged close to the chamber 16 and cooperates with the elements 34, 35 operating as overflow means. For this purpose the valve 33 cooperates with a tube 34, the end 35 of which draws from the chamber 16 at an intermediate point between ends 32, 32' . . . 32n of the tubes 29, 29' . . . 29n, and the end 22 of tube 21. The tube 36, connected to the outlet of valve 33, leads to the drain (not shown). An output 37 of the programmer 7 is connected to the valve 33 for actuation thereof. The tube 21 is connected to the flow cell 38 within the colorimeter 23, which also contains a light source 39, a condenser 40 and a photodetector 41. The flow cell 38 is connected to the tube 42, which enters into the chamber 43 through the cover 44. Said chamber 43 and said cover 44 are sealingly assembled together, i.e. in such a way as to enable an overpressure or a negative pressure to be maintained therein. The end 45 of the tube 42 is located inside the chamber 43. The bottom of the chamber 43 is connected by means of the tube 47 to the four-way valve 4. When the switch member 10 in the valve 4 is in position 13, it is connected to drain 49 by means of tube 48; when the switch member 10 is in position 14, while the switch member 9 is in position 12, the circuit is not in fluid communication with the outside or environment where the apparatus operates.

With reference to the above description, the operation of the apparatus according to the present invention will now be detailed. Liquid is taken up by the sampling thief 1 submerged in the flask 2, or in direct contact with the sample to be analyzed, under the action of the peristaltic pump 18. In this position the switch member 9 of valve 4 is in position 11, so that tube 3 is connected with tube 15. Following actuation of the peristaltic pump 18 in a clockwise direction (as defined hereinabove) the sample begins to flow into the chamber 16, until reaching a level corresponding to the end 22 of the tube 21. During this stage the valve 24 is open. Following this, through tube 21 and valve 24, the sample reaches the colorimeter 23. The liquid flows through the tube 21 until reaching chamber 43, and, through tube 47, reaches the valve 4 once again. The switch member 10 is in position 13, connecting tube 47 to the drain by means of tube 48. In this way, a first washing of the apparatus is performed. For an optimal functioning of the apparatus, the level of the liquid in chamber 16 should be equal to that defined by the end 35 of tube 34. In order to reach this level in chamber 16, the valve 24 is closed and the valve 33 is opened. As a consequence of this, under the action of the peristaltic pump 18 which pumps in a clockwise direction, the liquid flows continuously into chamber 16 until reaching the level defined by the end 35 of tube 34. Once this level has been reached, the overflow valve 33 discharges the excess liquid through end 36 of tube 34 into the drain. At this point, by operating outputs 26 and 37 of the programmer 7, the valve 33 is closed and the valve 24 is opened. The pump 18 continues to suck up the sample through the sampling thief 1 for a time sufficient to guarantee the presence of sample alone within the circuit of the apparatus in question. At this point the pump 18 is turned off and at the same time, by means of the programmer 7, the motor 5 moves the switch member 10 from position 13 to position 14 and the switch member 9 from position 11 to position 12, thus setting the apparatus for the measure. As the whole circuit of the apparatus according to the present invention is now completely filled with the sample, measurement of the "sample blank" can be performed, because the flow cell 38 of the colorimeter 23 is completely filled with said sample. For the determination of the analytes contained in the sample, it is now necessary to add reagents. For this purpose, the cut-off valve 24 is closed, and the peristaltic pump 18 is actuated in an counterclockwise direction. Part of the sample contained in the chamber 16 is displaced through the four-way valve 4, which is in a measuring position, until reaching chamber 43. In this way, the liquid is displaced from chamber 16 to chamber 43 without any sample flowing through the inside of the colorimeter 23. Once the liquid inside the chamber 16 has reached the level 6, the pump 18 is stopped. A negative pressure has been set inside the chamber 16 and an overpressure has been produced inside the chamber 43. The valve 30 is opened and the negative pressure inside the chamber 16 causes the dispensing of a metered amount of reagent $R_1$ or calibrator contained in the compartment 28 into said chamber 16. By means of the output 31 of the programmer 7, the opening time of the valve 30 is adjusted, causing dispensing of a metered amount of reagent $R_1$ or calibrator $C_1$ according to the type and assumed concentration of analyte under investigation. The addition of reagent and/or calibrator within the chamber 16 through the tube 29 produces a reduction of the negative pressure within the chamber 16 and, in order to restore said negative pressure, the peristaltic pump 18 is once again actuated in a counterclockwise direction until level 6 is once again restored inside chamber 16. Following this, and according to the type of analyte, the valve 30' is opened for a period of time sufficient to dispense the required amount of reagent for performance of the measurement reaction. Said reagent $R_2$ (or calibrator) is transferred from compartment 28' through tube 29', to the inside of the chamber 16. Once all the required reagents have been delivered inside the chamber 16, the peristaltic pump 18 is actuated in a clockwise direction until the liquid within chamber 16 reaches level 35. In case a calibration has to be performed a metered quantity of high concentrated calibrant is dispensed in chamber 16 before any reagent injection. The necessary steps for dispensing a calibrant from a calibrant container into the chamber 16 are the same as described for reagents.

According to a further embodiment of the apparatus according to the present invention, the reagents and/or calibrators are kept under pressure in the compartments 28, 28' 28n. The pressurization in the reagent compartments, upstream of the valves 30, 30' . . . 30n, provides an additional guarantee for the working of the injection system.

Following introduction of the reagents into the circuit of the apparatus according to the present invention, the overall volume of liquid contained inside the apparatus is increased by an amount equal to the sum of the amounts of reagents dispensed, thus causing a consequent increase of pressure within the system. To restore the pressure level existing prior to addition of the reagents and/or calibrators, the switch member 10 of valve 4 is switched from position 14 to position 13, that is to say to drain 49. The excess pressure inside the chambers 16 and 43 is eliminated by means of expulsion from chamber 43 towards the drain 49 of an amount of sample equal to the amount of reagents delivered in chamber 16. The switch member 10 of valve 4 is then displaced, again by the action of motor 5, from position 13 to position 14. The reagents delivered during the preceding stage in chamber 16 are partially diluted in the sample inside chamber 16 itself. The peristaltic pump 18 is actuated in a clockwise direction and the circulation of the sample and the reagents begins, allowing a rapid and efficient mixing to take place especially in chamber 16 where a high turbulence level is produced because the axis of tube 21 is not aligned with the bottom input of chamber 16.

The variation in absorbancy due to the appearance of reaction products and/or to the disappearance of reagents following development of the chemical reaction, is constantly measured, being the flow cell 38 of the colorimeter 23 within the circuit of the apparatus.

In this connection it should be underlined that arrangement of the apparatus according to the present invention makes it possible to take quantitative readings at any stage of development of the reaction, in view of the fact that the flow cell is within the circuit of the apparatus, so that a continuously repeated circulation of the liquid sample takes place within said cell. This arrangement, which makes it possible to follow the development of the reaction from the starting point to completion, is a unique characteristic for chemical analysis systems with flow cells. In the case of the prior art apparatuses indicated previously, both the analyzers using the analytical principle of Continuous Flow Analysis and those using the Flow Injection Analysis principle provide arrangements of instruments in which the detector is always downstream of the point at which reagents are introduced. Consequently the reading by the detector takes place when the reaction has already started, or when it has already ended, the detector being in no case arranged inside a closed measurement circuit. On completion of the reaction, the apparatus is adjusted for discharge of the liquid sample contained therein, by displacing, after operation of the motor 5, the switch member 10 of the valve 4 from position 14 to position 13 and, at the same time, actuating the peristaltic pump 18 in a clockwise direction. The switch 9 is set to position 11 and is connected by means of tube 3 to the sample or to a supply of washing liquid which thus allows the cleaning of the instrument, while the previous reaction product is being discharged through the tube 48 towards the drain 49.

The apparatus according to the present invention is once again filled with the sample, which is sucked up by means of the sampling thief 1, following actuation of the pump 18 in a clockwise direction with switch member 9 of valve 4 set to position 11. The chamber 16 is once again filled up to level 35. The sample flows through tube 21 until reaching the flow cell, passes through it and reaches chamber 43, pushing the previous reaction product towards the drain. In a very short time the circuit of the apparatus is completely filled with the new sample, and all traces of the previous reaction product have been eliminated. The return to conditions of absence of reaction product can easily be checked by reading data from the colorimeter. At this point the circuit is ready to perform a new cycle of analysis.

Figure 2:
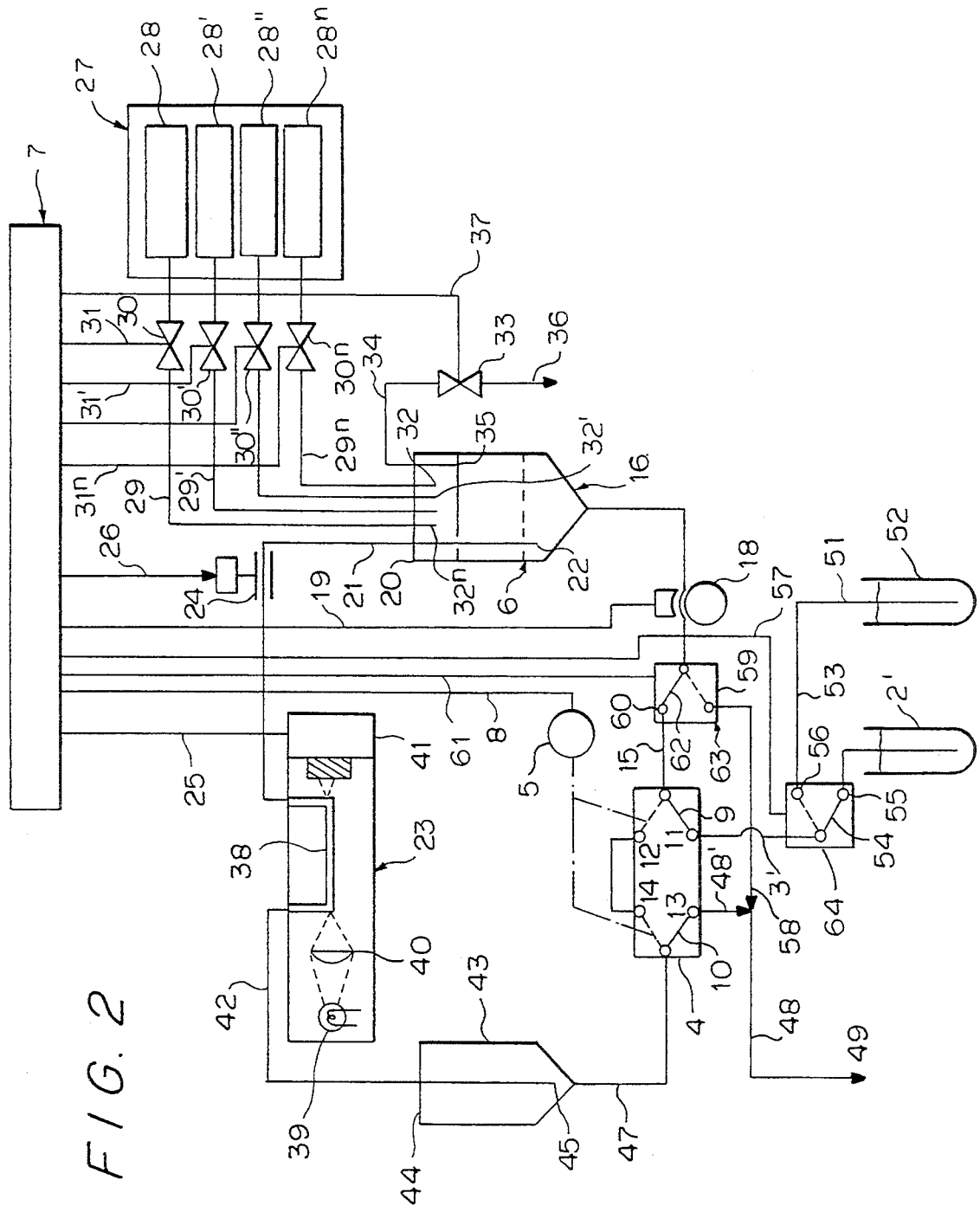
FIG. 2 shows a schematic view of the apparatus shown in FIG. 1, with a device for the taking of samples and for washing the circuit.

An alternative version of the apparatus according to the present invention will now be described, with reference to FIG. 2.

Between valve 4 and the peristaltic pump 18, a two-way valve 63 is positioned. In said valve 63, the switch member 62, controlled by the output 61 of the programmer 7, switches between positions 59 and 60.

When the switch member 62 is in position 60, the valve 4 and the chamber 16 are in communication; when the switch member 62 is in position 59, the chamber 16 is in communication with the drain 49 through the tube 58 which is connected to the tube 48. A two-way valve 64 is connected to position 11 of valve 4 by means of the tube 3'. The switch member 54 (controlled by output 57 of the programmer 7) of said valve 64 switches between positions 55 and 56. When the switch member 54 is in position 56, the circuit of the apparatus according to the present invention is connected to the flask 52 (or other equivalent recipient) containing washing liquid; when the switch member 54 is in position 55, the circuit of the apparatus according to the present invention is connected to the flask 2' (or other equivalent container) holding the sample with the analytes to be determined. Without departing from the scope of the present invention, it is also possible to provide for solutions, which are obvious to a person skilled in the art, in which the containers holding washing liquid and/or sample with analytes to be determined are more than one.

The operation of this apparatus will now be described in greater detail.

After determination of the analyte or analytes has been performed according to the description given hereabove, evacuation of the circuit of the apparatus according to the present invention is performed. The valve 24 is closed and the valve 33 is opened; the switch member 62 in the valve 63 is set to position 59. In this arrangement the chamber 16 is connected to the drain 49 by means of tubes 58 and 48 and, under the action of the peristaltic pump 18, which pumps in an counterclockwise direction, the contents of chamber 16 are evacuated.

With the switch member 54 in position 55, the switch member 9 in position 11 and the switch member 62 in position 60, under the action of the peristaltic pump 18, which pumps in a clockwise direction, sample is sucked up from flask 2' and delivered into the circuit. The sample flows into chamber 16 until reaching level 35, as the valve 24 is still closed and the valve 33 is open. The liquid flowing above level 35 is expelled through the drain 36. At this point the valve 24 is opened and valve 33 is closed; the liquid begins to flow through the inlet 22 of tube 21, through the colorimeter 23, the chamber 43 and the tube 47, pushing the product of the preceding reaction towards the drain. In this condition the switch member 10 of valve 4 is in position 13. With the switch member 54 of valve 64 in position 56 it is possible, as an alternative to suction of the sample from flask 2' to suck up a washing liquid from flask 52. After passing through chamber 16, cut-off valve 24, detector 23 and chamber 43, the washing liquid reaches valve 4, in which switch member 10 is in position 13 and which is in turn connected, by means of tubes 48' and 48, to the drain 49. In this way washing of the measuring circuit and measurement of the instrument blank is performed.

Moving the switch member 54 to position 55 the circuit is put into communication with the container 2' for start of the operation for the determination of the analyte or analytes according to the description given hereabove.

In spite of the fact that the invention has been described in detail herein, it is to be understood that said description is a non-limiting illustration, and embodiment changes can be made in practice by an expert in the field without departing from the scope of protection of the present invention.

I claim:

1. Apparatus for determining analytes in liquid samples which comprises
   a) means for sampling;
   b) bidirectional pump means in fluid connection with said means for sampling;
   c) an injection chamber in fluid connection with said pump means, through a bottom input, said injection chamber comprising a first outlet tube which draws to an inside thereof;
   d) means for controlling addition of at least one reagent and calibrator into said injection chamber while in fluid connection with said injection chamber;
   e) means for determining concentration of said analytes, in fluid connection with said injection chamber through said first outlet tube;

f) means for interrupting the fluid connection between said injection chamber and said means for determining the concentration of analytes;

g) an expansion chamber in fluid connection with said means for determining concentration, through an inlet tube which draws to an inside thereof, said expansion chamber comprising a second outlet tube;

h) means for discharging and recirculating the liquid samples in fluid connection with said expansion chamber through said second outlet tube and with said means for sampling and i) means for operating and controlling the apparatus, wherein said means for controlling addition is responsive to the fluid flow from said injection chamber to said expansion chamber, whereby said apparatus operates as a single hydraulic circuit closed to the external air.

2. Apparatus according to claim 1, wherein said means for sampling is formed by a three-way valve.

3. Apparatus according to claim 2, wherein said means for sampling is connected to a switch valve outside said apparatus.

4. Apparatus according to claim 1, wherein said bidirectional pump means are constituted by a positive displacement pump.

5. Apparatus according to claim 1, wherein said injection chamber is a fixed volume chamber capable of maintaining a depressure in an inside thereof, caused by said bidirectional pump means, thereby initiating delivery of reagent or calibrator.

6. Apparatus according to claim 1, wherein in said injection chamber said bottom input and said first outlet tube are offset so that when said bidirectional pump means deliver the analytes containing liquid sample to said injection chamber, a turbulent mixing with said at least one reagent and calibrator is provoked.

7. Apparatus according to claim 6, wherein said injection chamber is provided with overflow means.

8. Apparatus according to claim 1, wherein said means for the controlling addition of at least one reagent and calibrator are constituted by a number of separate compartments, each one containing a reagent or a calibrator, connected to said injection chamber.

9. Apparatus according to claim 8, wherein a respective valve is associated to each of said at least one reagent and calibrator compartments, to control the delivery thereof.

10. Apparatus according to claim 9, wherein in each compartment the respective reagent or calibrator kept under pressure.

11. Apparatus according to claim 1, wherein said means for interrupting the fluid connection are formed by cut-off valve.

12. Apparatus according to claim 1, wherein said means for determining the concentration of the analytes are constituted of one of a photometric and colorimetric detectors.

13. Apparatus according to claim 1, wherein at least one element of a group comprising of reduction columns, thermostated coils, dialysis units, distillation columns and ionic exchange resins is arranged to cooperate with said means for determining the concentration of analytes.

14. Apparatus according to claim 1, wherein said expansion chamber is fixed volume chamber, capable of maintaining in an inside thereof an overpressure, caused by the action of said bidirectional pump means.

15. Apparatus according to claim 1, wherein said means for discharging an recirculating liquid samples are constituted by a three-way valve.

16. Apparatus according to claim 15, wherein said means for discharging and recirculating liquid samples further comprise a two-way valve situated between said means for sampling and said pump means.

17. Apparatus according to claim 1, wherein said means for sampling and said means for discharging and recirculating liquid samples are arranged in a same unit.

* * * * *